US00PP22499P2

(12) United States Plant Patent
Kordes

(10) Patent No.: US PP22,499 P2
(45) Date of Patent: Feb. 21, 2012

(54) SHRUB ROSE PLANT NAMED 'KORJUKNEI'

(50) Latin Name: *Rosa hybrida*
Varietal Denomination: KORjuknei

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/925,246

(22) Filed: Oct. 14, 2010

(51) Int. Cl.
*A01H 5/00* (2006.01)

(52) U.S. Cl. ..... Plt./107

(58) Field of Classification Search ..... Plt./107
See application file for complete search history.

*Primary Examiner* — Kent L Bell

(57) ABSTRACT

A new and distinct variety of rose with long lasting, novel pink flowers, and attractive foliage with good disease resistance. It exhibits arching growth with abundant flowers. The new variety propagates well by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORjuknei'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2000. The crossing was between an unnamed seedling and another unnamed seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORjuknei'.

SUMMARY OF THE INVENTION

The new rose plant may be distinguished from its seed parent, an unnamed seedling, by the following combination of characteristics:

1. Length of and average leaf of 'KORjuknei' is 120 mm on average. Length of an average leaf of the unnamed seedling is 60-70 mm on average.
2. The growth habit of 'KORjuknei' is arching. The growth habit of the unnamed seedling is upright.

The new rose plant may be distinguished from its pollen parent, an unnamed seedling, by the following combination of characteristics:

1. The common flower color of 'KORjuknei' is pink. The common flower color of the unnamed seedling is cream-white.
2. The common foliage color of 'KORjuknei' is medium green. The common foliage color of the unnamed seedling is dark green.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORjuknei' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORjuknei' was selected in May, 2001 from the seedling beds to be asexually propagated for further evaluation. The first asexual propagation of 'KORjuknei' was done by budding to seedling understocks in July, 2001 at the inventor's nursery in Offenseth-Sparrieshoop, Germany.

This initial and other subsequent propagations conducted in controlled environments demonstrate that 'KORjuknei' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, flowers, leaves, and stems of 'KORjuknei'.

DETAILED BOTANICAL DESCRIPTION

The following is a description of 'KORjuknei', as observed growing in October, 2010 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORaburg', a rose variety from the same inventor described and illustrated in U.S. Plant Pat. No. 17,763 and issued on May 29, 2007 are compared to 'KORjuknei' in Chart 1.

CHART 1

| Characteristic | 'KORjuknei' | 'KORaburg' |
|---|---|---|
| Growth habit | Arching | Compact |
| Petal count | 100-120 | 26-40 |
| General tonality of open flower | Red Group 38C | Red-Purple Group 58C |

Parents:

*Seed parent.*—An unnamed seedling.

*Pollen parent.*—An unnamed seedling.

Classification:

*Botanical classification.*—*Rosa hybrida,* 'KORjuknei'.

*Commercial classification.*—Shrub rose.

FLOWER AND FLOWER BUD

Blooming habit: Recurrent.

Flower bud:

*Size.*—Upon opening, 30 mm in length from base of receptacle to end of bud and 20 mm diameter at its widest point.

*Bud form.*—Short. Pointed ovoid.

*Bud color.*—As sepals first unfold, bud color is Red Group 37C. When ¼ open, the upper surface of petals is Orange Group 27A, and the lower surface is Red Group 36B.

*Sepals.*—Size: Average 35 mm long×7 mm wide. Shape: Sepals generally acuminate. Sepal apex is generally cirrose. Weak foliaceous appendages on three of the five sepals. Base is flat at union with receptacle. Quantity: Five. Margins: Ciliated with stipitate glands. Surface texture: Inner side: Covered in fine hairs. Outer surface: Smooth. Stipitate glands are present. Color: Upper surface: Green Group 138B. Lower surface: Yellow-Green Group 146A.

Receptacle:

*Surface.*—Smooth. With stipitate glands.

*Color.*—Yellow-Green Group 144A.

*Shape.*—Funnel-shaped.

*Size.*—12 mm (h)×10 mm (w).

Peduncle:

*Surface.*—Smooth. With fine hairs and stipitate glands.

*Length.*—40 mm average length.

*Diameter.*—3 mm average diameter.

*Color.*—Yellow-Green Group 144A.

*Strength.*—Strong.

*Borne.*—Singly. 1-2 buds per flowering stem.

Flower bloom:

*Fragrance.*—Moderate.

*Duration.*—On the plant 8-10 days. Long lasting. As a cut flower, 6 to 8 days. Senesced petals drop away cleanly.

*Size.*—Large flowered garden rose. When open, the average flower diameter is 100 mm and the average flower height is 40 mm.

*Form.*—Shape of flower when viewed from the side: Upon opening, upper part: Flattened convex. Upon opening, lower part: Flattened concave. Open flower, upper part: Flattened convex. Open flower, lower part: Flat.

Color:

*Upon opening, petals.*—Outermost petals: Outer Side: Red Group 38D. Inner Side: Red Group 36D. Innermost petals: Outer Side: Red Group 38B. Inner Side: Red Group 49D.

*Upon opening, basal petal spots.*—Basal petal spot, outermost petals: Outer Side: Yellow-Green Group 144D. Inner Side: Yellow-Green Group 144D. Basal petal spot, innermost petals: Outer Side: Yellow-Green Group 144D. Inner Side: Yellow-Green Group 144 D.

*After opening, petals.*—Outermost petals: Outer Side: Red Group 36C. Inner Side: Red Group 36D. Innermost petals: Outer Side: Red Group 49B. Inner Side: Red Group 37D.

*After opening, basal petal spots.*—Basal petal spot, outermost petals: Outer Side: Yellow-Green Group 144D. Inner Side: Yellow-Green Group 150D. Basal petal spot, innermost petals: Outer Side: White Group 155D. Inner Side: White Group 155A. Variegations: None.

General tonality: On open flower, Red Group 38C. No change in the general tonality at the end of the 6$^{th}$ day. Afterwards, general tonality is Red Group 38D.

Petals:

*Petal count.*—Approximately 100-120 petals under normal conditions.

*Petal reflex.*—Petals reflex slightly.

*Petal edge.*—Entire.

*Petal shape.*—Deltoid. Apex shape is round. Shape of base is acute.

*Petal size.*—40 mm long; 40 mm wide.

*Thickness.*—Average.

*Petal arrangement.*—Generally in a regular pattern with overlapping edges.

Petaloids: Present.

*Petaloid count.*—Average of 40-60 per flower.

*Petaloid edge.*—Entire.

*Petaloid texture.*—Smooth.

*Petaloid shape.*—Deltoid.

*Petaloid size.*—Petaloids are 12 mm long and 4 mm wide.

*Petaloid color.*—Color of inner side is Red Group 38A. Color of outer side is Red Group 38A.

Reproductive organs:

*Pistils.*—Approximately 30 present. Stigmas: Location: Slightly inferior in position to anthers. Color: Green-Yellow Group 1C. Styles: Length: 9 mm long. Color: Green-Yellow Group 1C.

*Stamens.*—Approximately 30-40 on average and regularly arranged. Anthers: Size: 1-2 mm long. Color: Red Group 38D. Pollen: Generally absent. Filaments: Color: Green-Yellow Group 1D. Length: 10 mm.

THE PLANT

*Plant growth.*—Moderate vigor. Arching habit. When grown as a budded nursery plant the average plant height is 110 cm and the average plant width is 80 cm.

*Stems.*—Stem color: Young wood: Yellow-Green Group 144A. Older wood: Yellow-Green Group 144A. Stem surface: Young wood: Smooth. Older wood: Smooth.

*Prickles.*—Present. Incidence: 30-40 per 10 cm of young stem. 20-25 per 10 cm of old stem. Size: Average length: 5 mm. Color: Immature prickles: Gray-Red Group 181A. Mature prickles: Gray-Brown Group N144D. Senescing to Gray-Brown Group 199C. Shape: Concave. Anthocyanin: Color Gray-Red Group 181A.

*Leaves and leaflets.*—Normally 5 leaflets on normal leaves in middle of the stem. Venation pattern: Pyramidal net pattern. Leaf size: 120 mm (1)×100 mm (w). Quantity: Abundant. Texture: Upper side of leaflet: Semi glossy. Leathery. Under side of leaflet: Matte. Leathery. Color, mature foliage: Upper Leaf Surface: Green Group 137A. Lower Leaf Surface: Green Group 137D. Color, juvenile foliage: Upper Leaf Surface: Yellow-Green Group 147A. Lower Leaf Surface: Yellow-Green Group 147B. Anthocyanin intonation: Present. Location: Intonations present on juvenile leaf margins, developing leaves, peduncles, and stems. Color: Gray-Purple Group 183B.

*Stipules.*—Size: 25 mm long. 8 mm between the tips of the stipule. Main body of stipule 3-4 mm in width. Shape: Winged along middle. Stipule color: Yellow-Green Group 144A. Anthocyanin: Gray-Purple Group 183A. Presence of stipitate glands: Present on margins. Margins: Ciliate along the upper margins.

*Petiole.*—Length: 30 mm. Diameter: 3 mm. Petiole color: Yellow-Green Group 144A. Underneath: A few small prickles underneath. Stipitate glands: Limited numbers of stipitate glands on margins.

*Petiole rachis.*—Length: 40 mm. Diameter: 2-3 mm. Color: Yellow-Green Group 144A. Margins: Ciliated with a limited number of stipitate glands. Prickles: A few small prickles underneath. Stipitate glands: Limited numbers of stipitate glands on margins.

*Leaflets.*—Size: Average size of the terminal leaflet is 65 mm (1)×35 mm (w). Shape: Ovate. Base: Ovate. Apex: Acute. Margins: Serrated. Texture: Thick. Leathery.

Hips/seed formation: Observed. Size: 25 mm (1) and 25 mm (w). Color: Yellow-Green Group 144C.

Winter hardiness: To date, the variety has been grown successfully in Zone 5.

Disease resistance: Above average resistance to Powdery mildew (*Sphaerotheca pannosa*), rust (*P. disciflorum*), blackspot (*Diplocarpon rosae*), and Botrytis (*Botrytis cinerea*) diseases under normal growing conditions.

I claim:

1. A new and distinct variety of rose plant, as described and illustrated herein.

* * * * *

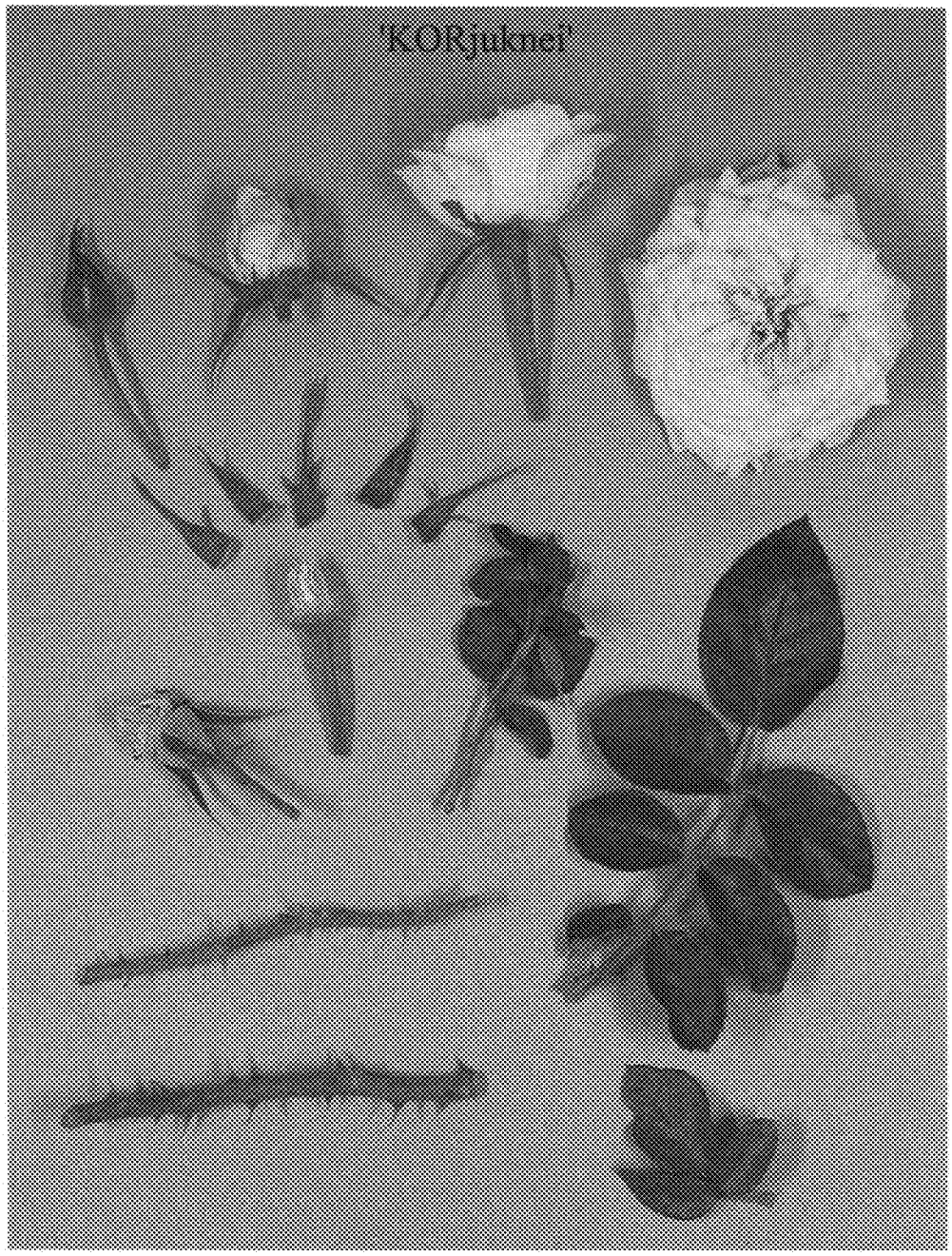
'KORjuknei'